United States Patent
Oshita et al.

(10) Patent No.: US 11,840,343 B2
(45) Date of Patent: Dec. 12, 2023

(54) AIRCRAFT SEAT AND SEAT MANAGEMENT SYSTEM

(71) Applicant: JAMCO CORPORATION, Tokyo (JP)

(72) Inventors: Toshihiko Oshita, Tokyo (JP);
Hiroyuki Hozumi, Tokyo (JP);
Tsuyoshi Oguri, Tokyo (JP);
Shinnosuke Kubota, Tokyo (JP)

(73) Assignee: JAMCO CORPORATION, Tokyo (JP)

( * ) Notice: Subject to any disclaimer, the term of this patent is extended or adjusted under 35 U.S.C. 154(b) by 652 days.

(21) Appl. No.: 17/063,895

(22) Filed: Oct. 6, 2020

(65) Prior Publication Data
US 2021/0107660 A1 Apr. 15, 2021

(30) Foreign Application Priority Data

Oct. 11, 2019 (JP) ................................. 2019-187388

(51) Int. Cl.
*B64D 11/06* (2006.01)
*A61B 5/00* (2006.01)

(52) U.S. Cl.
CPC ........ *B64D 11/0641* (2014.12); *A61B 5/6887* (2013.01); *B64D 11/0647* (2014.12); *B64D 11/0606* (2014.12); *B64D 11/0638* (2014.12)

(58) Field of Classification Search
CPC ............ B64D 11/0641; B64D 11/0647; B64D 11/0606; B64D 11/0638; B64D 11/0626; A61B 5/6887; B60N 2/665
See application file for complete search history.

(56) References Cited

U.S. PATENT DOCUMENTS

| | | | |
|---|---|---|---|
| 6,098,000 A * | 8/2000 | Long | A47C 4/54 307/10.6 |
| 9,022,320 B2 * | 5/2015 | Wallace | B64D 11/0646 244/118.6 |
| 9,889,770 B2 | 2/2018 | Hotary et al. | |
| 10,799,666 B2 | 10/2020 | Tomiyama et al. | |
| 2002/0113477 A1 | 8/2002 | Uchiyama | |
| 2009/0273213 A1 * | 11/2009 | Mukherjee | B64D 11/06395 297/217.3 |

(Continued)

FOREIGN PATENT DOCUMENTS

| | | | |
|---|---|---|---|
| DE | 102017212791 A1 * | 2/2018 | ......... B60H 1/00285 |
| EP | 3395684 A1 * | 10/2018 | ......... B64D 11/0007 |

(Continued)

*Primary Examiner* — Michael J Zanelli
(74) *Attorney, Agent, or Firm* — Renner, Otto, Boisselle & Sklar, LLP (57) ABSTRACT

Provided is an aircraft seat that enhances passenger comfort and reduces the burden on cabin attendants. The aircraft seat includes a base with a relatively movable seat portion and a backrest portion; an actuator for relatively moving the seat portion and the backrest portion; a biometric sensor installed on the base and configured to obtain biometric information of a passenger; a plurality of elastic members installed on the base; a modification device configured to change an elastic force of at least one elastic member, and a control device, wherein the control device operates the actuator or the modification device in response to a signal from the biometric sensor.

5 Claims, 5 Drawing Sheets

(56) References Cited

U.S. PATENT DOCUMENTS

2015/0008710 A1    1/2015  Young et al.
2016/0339802 A1*  11/2016  Hanlon ................ B60N 2/0228
2020/0148364 A1*  5/2020  Vandewall ........... A61B 5/4815

FOREIGN PATENT DOCUMENTS

| EP | 3521166 A1 | 8/2019 | | |
|----|----|----|----|----|
| EP | 3530569 A1 | 8/2019 | | |
| JP | 2002-240598 A | 8/2002 | | |
| JP | 2016-199267 A | 12/2016 | | |
| JP | 2018079840 A | * | 5/2018 | |
| JP | 2018-86257 A | | 6/2018 | |
| WO | WO-2021123749 A1 | * | 6/2021 | ........... A61B 5/6887 |

\* cited by examiner

AIRCRAFT SEAT AND SEAT MANAGEMENT SYSTEM

CROSS-REFERENCE TO RELATED APPLICATIONS

The present application claims priority to Japanese Patent Application No. 2019-187388, filed Oct. 11, 2019. The contents of this application are incorporated herein by reference in their entirety.

BACKGROUND OF THE INVENTION

The present invention relates to an aircraft seat and a seat management system.

Among aircraft seats for first class and business class, various measures have been devised to allow passengers to spend flights comfortably.

SUMMARY OF THE INVENTION

In Japanese Unexamined Patent Application Publication No. 2002-240598 (Patent Document 1), an electric seat is disclosed that can be used as a chair for a passenger to sit on by angling the seat back and leg rest with respect to the seat cushion, or that can be used as a bed by making the seat back and the leg rest horizontal with respect to the seat cushion.

According to the electric seat of Patent Document 1, in response to a passenger's input of an operation switch, a controller drives an actuator to move the seat back and the leg rest, whereby the chair or the flat state can be achieved. However, in a case that a passenger falls asleep while sitting on the chair, the chair state is maintained, which may be a burden on the body of the passenger.

On the other hand, cabin attendants in aircraft are required to be aware of the condition of passengers, but the seats for first class and business class in modern aircraft are often provided with partitions that can be opened or closed in order to maintain the privacy of passengers. For this reason, when the partition is closed, it may be difficult for cabin attendants to check on the condition of passengers from the aisle side, and difficulties can arise.

Therefore, it is an object of the present invention to provide an aircraft seat and a seat management system that enhance passenger comfort while also making it easy for cabin attendants to check the condition of passengers as necessary.

In order to achieve the above object, an aircraft seat according to the present invention includes a base with a relatively movable seat portion and a backrest portion; an actuator for relatively moving the seat portion and the backrest portion; a biometric sensor installed on the base and configured to obtain biometric information of a passenger; a plurality of elastic members installed on the base; a modification device configured to change an elastic force of at least one elastic member, and a control device, wherein the control device operates the actuator or the modification device in response to a signal from the biometric sensor.

In addition, in order to achieve the above object, a management system for an aircraft seat according to the present invention includes the aircraft seat according to claim 1 and a plurality of terminals; wherein: one terminal is capable of transmitting setting information regarding the aircraft seat to a control unit of the aircraft seat, and another terminal is capable of receiving, from a control unit of the aircraft, information regarding a signal of the biometric sensor.

According to the present invention, it is possible to provide an aircraft seat and a seat management system that enhance passenger comfort while also making it easy for cabin attendants to check the condition of passengers as necessary.

DETAILED DESCRIPTION

Figure 1:
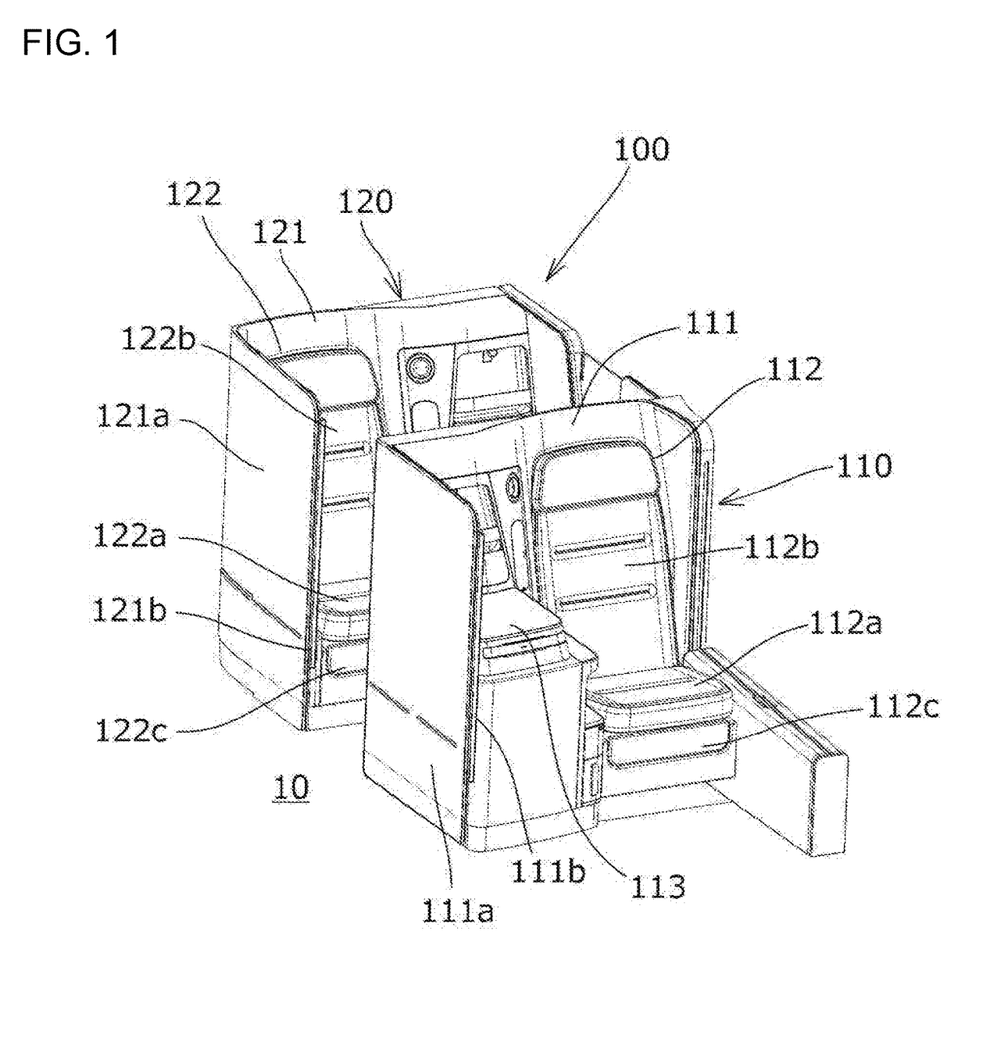
FIG. 1 is a perspective view of a seat structure according to an embodiment of the present invention as viewed from the front side.
Figure 2:
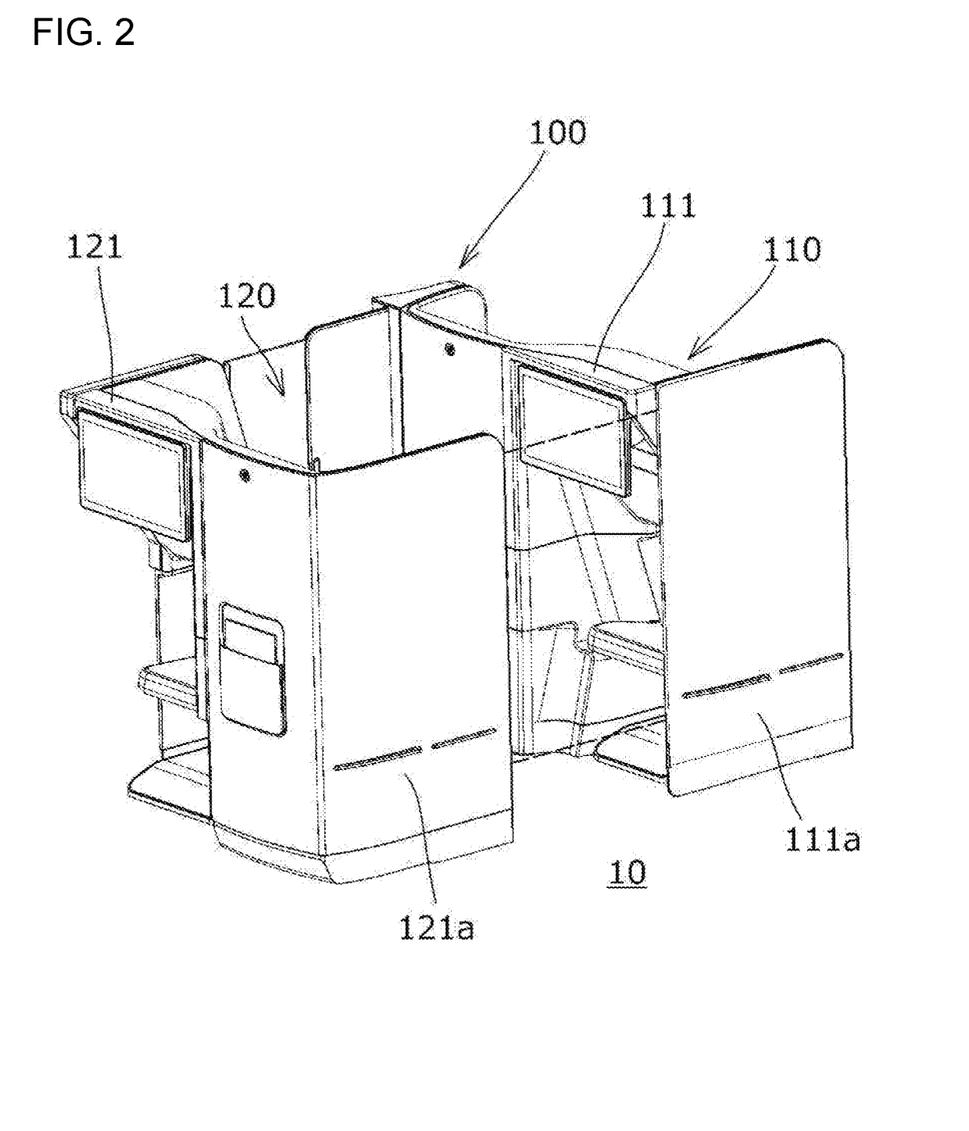
FIG. 2 is a perspective view of the seat structure according to the present embodiment as viewed from the rear side.
Figure 3:
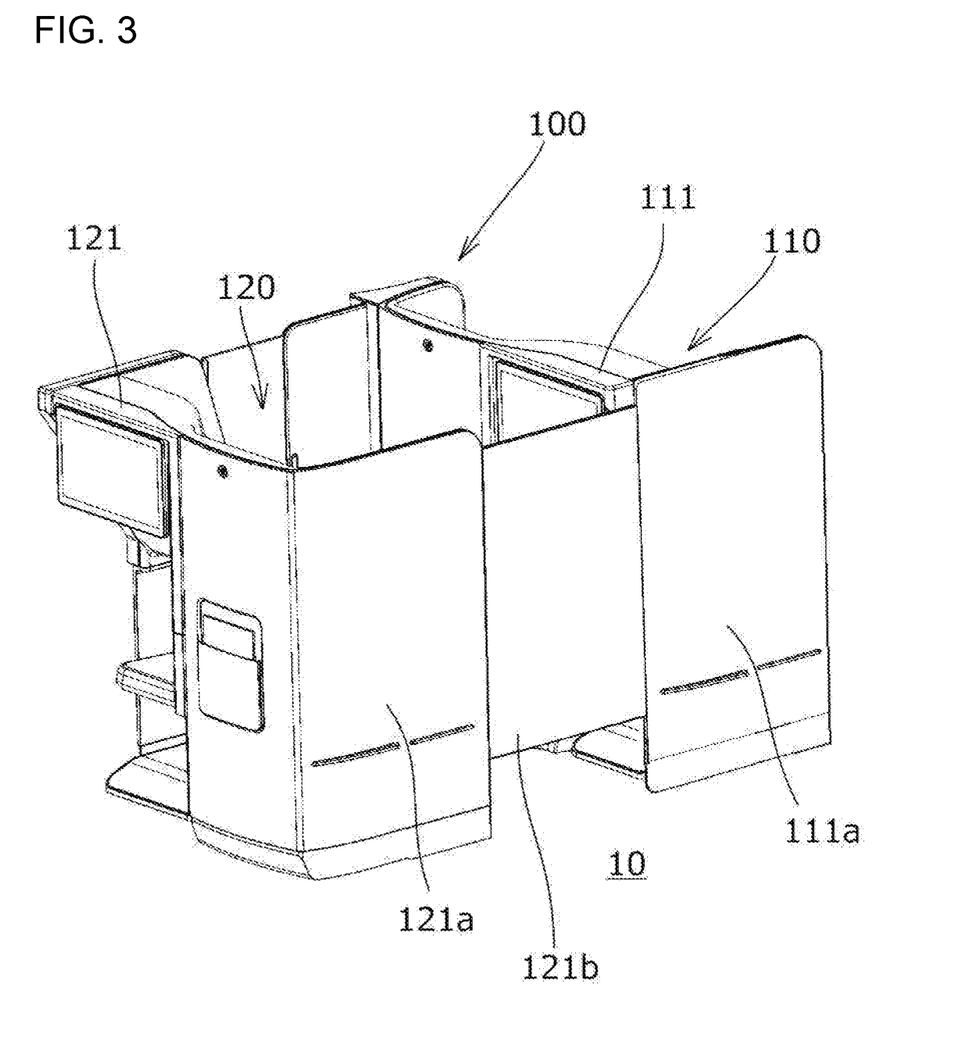
FIG. 3 is a perspective view of the seat structure according to the present embodiment as viewed from the rear side.

Hereinafter, an aircraft seat and a seat management system according to an embodiment of the present invention will be described with reference to the drawings. FIG. 1 is a perspective view of a seat structure 100 according to an embodiment of the present invention as viewed from the front side. FIG. 2 is a perspective view of the seat structure 100 according to the present embodiment as viewed from the rear side, and illustrates a state in which the door is open. FIG. 3 is a perspective view of the seat structure 100 according to the present embodiment as viewed from the rear side, and illustrates a state in which the door is closed.
(Configuration of Aircraft Seats)

In the present embodiment, the first seat unit 110 and the second seat unit 120 coupled to the rear side of the first seat unit 110 constitute one seat structure 100. In addition, a plurality of seat structures 100 are mounted in an aircraft.

In FIG. 1, the first seat unit 110 includes a seat 112 and a side table 113 inside a shell 111 made of resin. In addition, the second seat unit 120 also includes a seat 122 and a side table (not illustrated in the Figures) inside a shell 121 made of resin.

In the seat 112, a seat back 112b and a leg rest 112c are relatively pivotably connected to a seat cushion 112a. More specifically, the seat 112 can be form-changed between a seat state in which the seat back 112b stands erect and the leg rest 112c reclines vertically and a flat state in which the seat back 112b and the leg rest 112c approach a horizontal state.

In the seat 122 as well, a seat back 122b and a leg rest 122c are relatively pivotably connected to a seat cushion 122a. More specifically, the seat 122 can be form-changed between a seat state in which the seat back 122b stands erect and the leg rest 122c reclines vertically and a flat state in which the seat back 122b and the leg rest 122c approach a horizontal state. It should be noted that the leg rests 112c and 122c are not strictly necessary. Alternatively, the seat cushions 112a, 122a and the seat backs 112b, 122b may be fixed, and the leg rests 112c, 122c may be pivotably connected to them.

The shell 111 includes, on the side of the aisle 10 of the aircraft, a partitioning screen 111a that stands upright in parallel with the aisle 10. In addition, the shell 121 also includes, on the side of the aisle 10 of the aircraft, a partitioning screen 121a that stands upright in parallel with the passage 10. The partitioning screen 111a includes a slidable door 111b. The partitioning screen 121a also includes a slidable door 121b. FIG. 3 illustrates the door 121b in a closed state.

(Configuration of Seat Management System)

Figure 4:
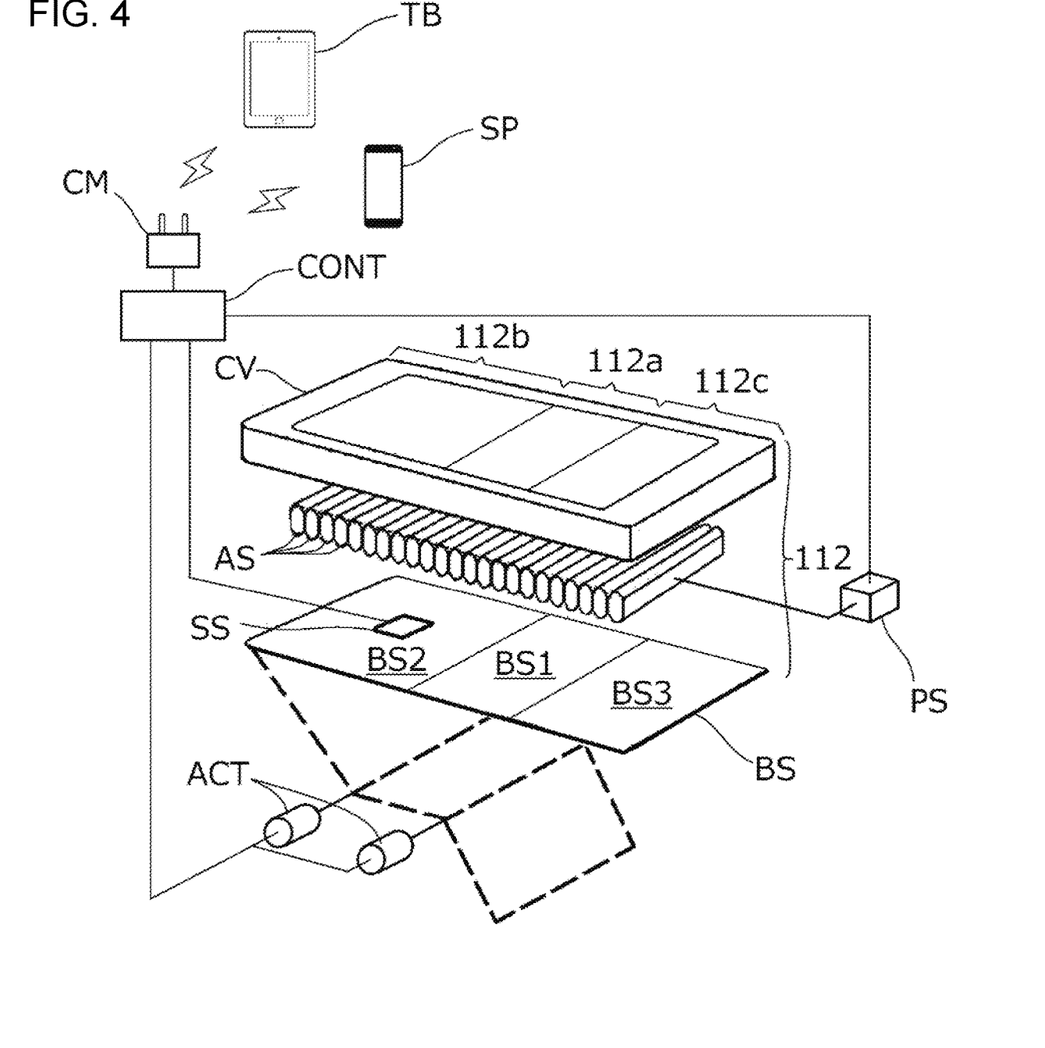
FIG. 4 is a schematic diagram of an entire seat management system including the seat structure according to the present embodiment.

FIG. 4 is a schematic diagram of an entire seat management system including seats. Here, the seat 112 will be described as an example, but the seat 122 has a similar configuration. The components that form the seat 112 are a base BS, air cells AS, an outer skin CV, and a biometric sensor SS. The base BS, which is made from metal plates, includes a first plate (a seat portion) BS1 that corresponds to the seat cushion 112a, a second plate (a backrest portion) BS2 that corresponds to the seat back 112b, and a third plate that corresponds to the leg rest 112c. BS3 and. The second plate BS2 and the third plate BS3 are pivotably supported with respect to the first plate BS1.

The second plate BS2 and the third plate BS3 are each connected to an actuator ACT, and the actuator ACT is connected to a control device CONT. When a drive signal for the chair state is transmitted from the control device CONT to the actuator ACT, the second plate BS2 and the third plate BS3 are angled with respect to the first plate BS1 (illustrated by the dotted lines in FIG. 4). As a result, the air cells AS and the outer skin CV also follow the base BS, and the chair state illustrated in FIG. 1 is achieved. It should be noted that the movements of the second plate BS2 and the third plate BS3 illustrated in FIG. 4 are merely examples, and the present invention is not limited to these.

On the other hand, when a drive signal for the flat state is transmitted from the control device CONT to the actuator ACT, the second plate BS2 and the third plate BS3 become horizontal (illustrated by the solid line in FIG. 4) with respect to the first plate BS1. As a result, the air cells AS and the outer skin CV also follow the base BS, and the seat 112 enters the flat (bed) state. When the drive signal is transmitted from the control device CONT to the actuator ACT, information regarding the transmitted drive signal is transmitted to the terminal TB, which will be described later.

It should be noted that the actuator ACT may be disposed within the seat 112, but it is preferable that the pump PS that will be described later be installed outside the seat 112, below the side table, for example. As a result, the pump PS does not need to satisfy the regulation value required for the seat, which contributes to allow more freedom of choice of the pump PS.

The biosensor SS is disposed at the center of the second plate BS2 that corresponds to the seat back 112b. A vibration sensor as described in Japanese Unexamined Patent Application Publication No. 2019-98068 can be used as the biological sensor SS, for example. The biometric sensor SS can detect vibrations emitted from the passenger using the seat 112 as a biometric signal (or biometric information), extract respiration, pulse, heart rate, and the like, and determine whether or not the passenger is in a sleep state, for example. At this time, the motion of the aircraft, the engine vibration, and the like can be eliminated by using an appropriate filter.

It should be noted that the biometric sensor SS is not limited to vibration, and any sensor that can be used to sense the condition of the passenger without contact can be used. However, the use of surveillance cameras and the like is often restricted because of problems related to passenger privacy. A biometric sensor that detects vibration as in the present embodiment is preferable because such privacy problems do not occur. It is also possible to use two or more biometric sensors SS.

The outer skin CV is made of a flexible resin material and covers the front surface and the side surface of the sheet 112.

The air cells AS that serve as elastic members are disposed between the base BS and the outer skin CV. Each of the air cells AS is a substantially cylindrical flexible bag with both ends closed, extends along the width direction of the first plate BS1, the second plate BS2, and the third plate BS3 of the base BS, and is arranged along the longitudinal direction of the base BS while being adjacent to each other. Each of the air cells AS is individually connected to a pump (a modification device) PS via a tube (not illustrated in the Figures).

The pump PS is connected to the control device CONT. By transmitting a drive signal from the control device CONT to the pump PS, each of the air cells AS is independently pressurized and expanded, or alternatively decompressed and contracted. When the drive signal is transmitted from the control device CONT to the pump PS, information regarding the transmitted drive signal is transmitted to the terminal TB, which will be described later. It should be noted that the number and shape of the air cells AS can be arbitrarily selected. In addition, the internal pressure of the air cells AS may be changed according to the internal pressure of the aircraft. Further, the elastic member is not limited to an air cell.

The control device CONT is connected to the communication device CM, such that it becomes possible to transmit information between a cabin attendant terminal (tablet) TB and a passenger operation terminal (a smartphone or the like) SP via the communication device CM. With regard to the communication of information between the communication device CM and the terminals TB and SP, WiFi communication is used in the present embodiment, but Bluetooth or other forms of wireless communication may be used, or wired communication may be performed. Although not illustrated in the Figures, in the case that an operation switch that can be operated by a passenger is provided for each seat, the signal of the operation switch is input to the control device CONT via the communication device CM in a wireless or wired manner together with the information of the corresponding seat.

(Operation of the Seat Management System)

The operation of the seat management system including the seat according to the present embodiment will be described below. It should be noted that, although the seat 112 will be described as an example here, the same applies to other seats.

An application provided by, for example, the airline company is preferably downloaded in advance to the terminal SP used by the passenger. When this application is executed, by scanning a QR code assigned to each seat, for example, the seat information is read out and access to the control device CONT is permitted, and subsequently it becomes possible to input the tilt angle of the seat back and leg rest or the hardness of the seat used by the user.

<1. Automatic Operation During Takeoff and Landing>

First, at the time of takeoff and landing of the aircraft, the control device CONT drives the actuator ACT automatically or by an operation of the terminal of the cabin attendant to put the seat 112 in the chair state. As a result, the passenger will enter a posture suitable for fastening the seat belt. After the aircraft has taken off, the passenger can access the control device CONT using his/her terminal SP (or the operation switch provided on the side table 113) to freely change the seat 112 from the chair state to the flat state or from the flat state to the chair state by driving the actuator ACT. In addition, it is also possible to stop the actuator ACT at an intermediate position between the chair state and the flat state and maintain the seat 112 in that state.

On the other hand, in a case that the landing time of the aircraft is approaching, the control device CONT drives the actuator ACT automatically or by an operation of the terminal of the cabin attendant to change the seat 112 from the flat state to the chair state. This prompts the passenger to wake up and be alerted that he or she is about to arrive. By gradually raising the seat back as the landing time of the aircraft approaches, it is possible to allow the passengers to wake up naturally rather than compulsorily.

<2. Setting the Preferred Seat Angle Using the Terminal>

In addition, if the passenger stores a value relating to his/her favorite seat angle in the built-in memory of the terminal SP, by transmitting this value from the terminal SP to the control device CONT, the passenger can set the seat back 112b and the leg rest 112c to a desired angle.

<3. Setting the Preferred Seat Hardness Using the Terminal>

Furthermore, the passenger can access the control device CONT using his/her terminal SP, drive the pump PS to adjust the elastic force of the air cells AS, and freely set the hardness of the seat 112. Generally, each individual passenger has a different seat hardness preference, but a common seat 112 is used during flights. Accordingly, the passenger can store a group of values corresponding to the internal pressures of the air cells AS in the built-in memory of the terminal SP in advance so that each passenger can have the hardness of his or her preference. By means of the passengers on board transmitting this group of values to the control device CONT, the control device CONT drives the pump PS in accordance with this transmitted group of values, and the internal pressures of the air cells AS of the seat 112 used by the passenger can be changed to a desired value. The internal pressure may be adjusted for each group formed by a plurality of adjacent air cells AS.

<4. Selection of Standard Seat Stiffness>

On the other hand, in anticipation of cases in which a passenger does not know the desired hardness of his or her seat, such as a passenger who uses the seat 112 for the first time, it is possible to preemptively set a plurality of stages of recommended settings such as "soft", "normal", and "hard", and store a group of values corresponding to each in the built-in memory of the control device CONT. In such a case, the passenger can access the control device CONT using his/her terminal SP (or the operation switch provided on the side table 113) and select any recommended setting. At this time, the control device CONT can drive the pump PS by reading the group of values corresponding to the recommended setting selected by the passenger from the built-in memory.

<5. Management of Health Conditions During Flight>

In addition, in response to the passenger's request, the control device CONT can also transmit information such as the breathing frequency, pulse, heartbeat, and the number of times the passenger turns over to the passenger's terminal SP, and display this information on the terminal SP. By viewing this display, the passenger can be aware of their health conditions during the flight.

<6. Monitoring and Automatic Operation of Sleep State>

During the flight, passengers may fall asleep with their seat in the chair state. In such a case, on the condition that the passenger has allowed automatic operation, the control device CONT detects the signal from the biometric sensor SS, and if it is determined that the passenger has fallen asleep despite the seat 112 being in the chair state, the actuator ACT is automatically driven to change the seat 112 from the chair state to the flat state. As a result, the passenger enters a lying state that has less strain on the body without being forced to remain in a sitting posture, such that comfortable sleep can be facilitated. As an example of a passenger allowing automatic operation in advance, the seat may be automatically moved only when the passenger has indicated their intention to allow automatic operation using an operation switch provided on the terminal SP or the side table 113.

<7. Sleep State Inducement Operation>

The control device CONT can also detect the signal from the biometric sensor SS and determine whether or not the passenger is relaxing and transitioning to a sleep state based on the depth of his or her breathing or the like, for example. In the case that the control device CONT determines that the passenger is not relaxed, it is possible for the control device CONT to automatically drive the actuator ACT to change the angle of the seat back 112b of the seat 112, or automatically drive the pump PS to adjust the internal pressure of the air cells AS, or to provide a slight vibration. As a result, the passengers sitting in each seat can be encouraged to fall asleep quickly. If the passengers all fall into the sleep state at the same time, the work burden of the cabin attendants can be reduced.

<8. Snoring Detection and Automatic Operation>

Similarly, the control device CONT can also detect the signal from the biometric SS and determine whether or not the passenger is snoring based on the magnitude of vibration during breathing, for example. In the case that the control device CONT determines that the passenger is snoring, it is possible for the control device CONT to automatically drive the actuator ACT to change the angle of the seat back 112b of the seat 112, or automatically drive the pump PS to adjust the internal pressure of the air cells AS. As a result, the snoring of passengers can be suppressed, and the comfort of passengers who use adjacent seats can be improved.

<Automatic Operation when Turbulence is Encountered>

On the other hand, when the aircraft is greatly shaken due to turbulence, for example, after making an announcement via an emergency in-flight broadcast indicating that seats 112 will be returned from the flat state to the chair state, the control device CONT can drive the actuator ACT automatically or based on a terminal operation of the cabin attendant to forcibly change the seats 112 from the flat state to the chair state. In this way, passenger safety can be ensured.

(Use of the Seat Management System by Cabin Attendants)

Figure 5:
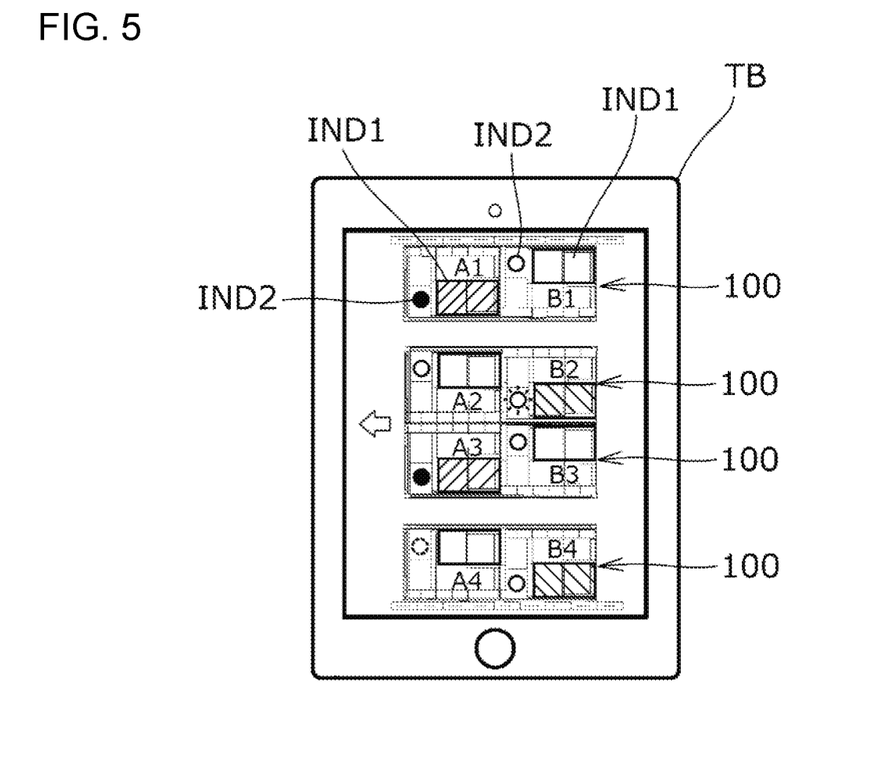
FIG. 5 is a diagram illustrating an example of a display of a terminal for cabin attendants according to the present embodiment.

FIG. 5 is a diagram illustrating an example of a display of a terminal TB for cabin attendants according to the present embodiment. On the display screen of the terminal TB, top view images of eight seats in the four sets of seat structures 100 and seat names (A1 to A4, B1 to B4) corresponding thereto are displayed. The number of seats displayed is arbitrary, and by flicking or swiping the display screen of the terminal TB, for example, the seat image of a desired position can be displayed.

The information transmitted from the control device CONT to the terminal TB includes the information regarding the drive signals of the actuator ACT and the pump PS, the information regarding the presence/absence of seat use based on the presence/absence of a biometric signal detected by the biometric sensor SS, and information regarding whether the passenger is awake or sleeping as determined based on the biometric signal detected by the biological sensor SS. Based on the information from the control device CONT, the first display IND1 and the second display IND2 are displayed independently for each seat. The arrow in the display indicates the nose side of the aircraft.

The first display IND1 indicates the state of the seat; for example, white is displayed for the chair state and gray (hatching in FIG. 5) is displayed for the flat state. On the other hand, the second display indicates the state of the passenger, and is hidden (illustrated with dotted lines in the Figures) when, for example, the passenger is not using the seat because he/she has gotten up to use the lavatory or the like (corresponding to "A4" in FIG. 5), and is displayed as a circular shape when the passenger is using the seat. Further, when the passenger is awake, the second display is a red circle display (shown in white in FIG. 5), and when the passenger is sleeping, the second display is a blue circle display (shown in black in FIG. 5).

In this way, since the first display IND1 and the second display IND2 are displayed on the display screen of the terminal TB based on the information from the control device CONT, it is possible for the cabin attendant to observe the condition of a plurality of passengers by glancing at the display screen of the terminal TB without patrolling the aircraft. In particular, in the case that the door 121b is closed as illustrated in FIG. 3 and the state of passengers inside is difficult to grasp by the cabin attendant from the outside, there is an advantageous effect of using the display of the terminal TB. This significantly reduces the burden on the cabin attendant during taxiing, takeoff and landing, and during flight. It should be noted that, in addition to this, for example, based on the information from the control device CONT, a display indicating the degree of relaxation (or tension) of passengers may be presented, for example.

In the display example of FIG. 5, the passenger using the seat "B4" continues to remain awake even though the seat is in a flat state. A cabin attendant who sees such a situation can call out to the passenger using the seat "B4" and confirm his or her health condition or the like. Depending on the symptoms of the passenger, it is possible to carry out an optimal treatment early, in cooperation with a doctor or a nurse waiting on the ground. In addition, by separately displaying the awake time and the sleep time of each passenger, it is possible the cabin attendant becomes mindful of the passenger status and may personally inquire if any service is required.

Further, in the display example of FIG. 5, when the passenger using the seat "B2" wakes up from sleep, the second display IND2 can be made to blink (and/or provide a voice message) based on the information from the control device CONT to notify the cabin attendant that the passenger is awake. As a result, the hospitality of the cabin attendant can be exhibited, for example, by providing drinks and meals that were put on hold while the passenger was asleep at the optimum timing, and the airline company's reputation can be enhanced.

Also, by accumulating information such as a service history for each passenger, it is possible to utilize technology such as AI to provide recommended information regarding service type and timing to cabin attendants.

The control device CONT can access the server of the airline company in real time or upon arrival to transfer the data of the biometric sensor SS in association with the aircraft route, aircraft type, flight time, seat position, and individual passenger information (sex, age, sleep time, or the like). By analyzing this data, it is possible to analyze, for example, the reason why passengers could not get enough sleep, which can lead to further improving the comfort of flights.

Although the aircraft seat according to the present embodiment has been described above, the present invention is unlimited to the specific examples described above, and various modifications can be made.

What is claimed is:

1. An aircraft seat comprising:
   a base with a relatively movable seat portion and a backrest portion;
   an actuator for relatively moving the seat portion and the backrest portion;
   a biometric sensor installed on the base and configured to obtain biometric information of a passenger;
   a plurality of elastic members installed on the base;
   a modification device configured to change an elastic force of at least one elastic member, and
   a control device,
   wherein, in response to a signal from the biometric sensor, the control device operates the modification device to encourage the passenger to sleep state, in case it is determined that the passenger is not in a sleep state, or drives the actuator and changes the backrest portion from a chair state to a flat state, in case it is determined that the passenger is asleep despite the backrest portion being in the chair state.

2. An aircraft seat according to claim 1, wherein;
   the control device detects a relaxing state of a passenger sitting on the seat, based upon the signal from the biometric sensor, and operates the modification device to change the elastic force of at least one elastic member, in response to the relaxing state.

3. An aircraft seat according to claim 1, wherein;
   a hardness of the seat can be adjusted by changing the elastic force of at least one elastic member.

4. An aircraft seat according to claim 1, wherein:
   the control device gradually raises the seat back portion as a landing time of the aircraft approaches.

5. An aircraft seat management system comprising:
   the aircraft seat according to claim 1 and a plurality of terminals;
   wherein:
   one terminal is capable of transmitting setting information regarding the aircraft seat to a control unit of the aircraft seat, and
   another terminal is capable of receiving, from a control unit of the aircraft, setting information regarding a signal of the biometric sensor.

* * * * *